US009494600B2

(12) United States Patent
Iwano et al.

(10) Patent No.: US 9,494,600 B2
(45) Date of Patent: Nov. 15, 2016

(54) METHOD FOR TESTING FOR NEPHRITIS-LESION SITES AND REAGENT THEREFOR

(71) Applicants: NATIONAL UNIVERSITY CORPORATION UNIVERSITY OF FUKUI, Fukui-shi, Fukui (JP); DS PHARMA BIOMEDICAL CO., LTD., Suita-shi, Osaka (JP)

(72) Inventors: Masayuki Iwano, Fukui (JP); Hiroyuki Funaoka, Suita (JP)

(73) Assignees: National University Corporation University of Fukui, Fukui (JP); DS Pharma Biomedical Co., Ltd., Suita (JP)

( * ) Notice: Subject to any disclaimer, the term of this patent is extended or adjusted under 35 U.S.C. 154(b) by 0 days.

(21) Appl. No.: 14/440,468

(22) PCT Filed: Nov. 8, 2013

(86) PCT No.: PCT/JP2013/080296
§ 371 (c)(1),
(2) Date: May 4, 2015

(87) PCT Pub. No.: WO2014/073653
PCT Pub. Date: May 15, 2014

(65) Prior Publication Data
US 2015/0268250 A1 Sep. 24, 2015

(30) Foreign Application Priority Data

Nov. 9, 2012 (JP) ................. 2012-247896

(51) Int. Cl.
*G01N 33/68* (2006.01)
*C07K 16/18* (2006.01)

(52) U.S. Cl.
CPC ........... *G01N 33/6893* (2013.01); *C07K 16/18* (2013.01); *G01N 33/68* (2013.01); *G01N 2333/4727* (2013.01); *G01N 2800/347* (2013.01)

(58) Field of Classification Search
None
See application file for complete search history.

(56) References Cited

U.S. PATENT DOCUMENTS

2013/0101592 A1   4/2013   Hernandez Miguez et al.

FOREIGN PATENT DOCUMENTS

WO   WO 2011/157724 A1   12/2011

OTHER PUBLICATIONS

Iwano et al., *J. Am. Soc. Nephrol.*, 23(2): 209-214 (2012).
Kim et al., *The Journal of Biological Chemistry*, 278(32): 30063-30073 (2003).
Nishitani et al., *The Japanese Journal of Nephrology*, 43(3): 246, abstract P-257 (2001).
Oslejskawa et al., *Rheumatology*, 48(12): 1590-1594 (2009).
Samejima et al., *Nephron. Clinical Practice*, 120(1): c1-c7, doi: 10.1159/000334184 (2012).
Yamaguchi et al., *American Journal of Kidney Diseases*, 54(4): 653-664 (2009).
Yamaguchi et al., *The Japanese Journal of Nephrology*, 52(3): 305, abstract 2-05-13 (2010).
European Patent Office, Extended European Search Report in European Patent Application No. 13852787.4 (May 9, 2016).
Japanese Patent Office, International Search Report in International Patent Application No. PCT/JP2013/080296 (Feb. 18, 2014).

*Primary Examiner* — Jacob Cheu
(74) *Attorney, Agent, or Firm* — Leydig, Voit & Mayer, Ltd.

(57) ABSTRACT

Provided is a method of measuring and comparing multimer FSP1 and monomer FSP1 by using an FSP1-specific antibody and the like.

12 Claims, 3 Drawing Sheets

Fig. 1

```
                        (F1-2)
                        1  MACPLEKALDVM
   1    2    3    4     2  PLEKALDVMVST
                        3  KALDVMVSTFHK
                        4  DVMVSTFHKYSG (I11-23)
   5    6    7    8   9 5  NEVDFQEYCVFL
                        6  DFQEYCVFLSCI
                        7  EYCVFLSCIAMM
                        8  VFLSCIAMMCNE
                        9  SCIAMMCNEFFEG
```

METHOD FOR TESTING FOR NEPHRITIS-LESION SITES AND REAGENT THEREFOR

CROSS-REFERENCE TO RELATED APPLICATIONS

This patent application is the U.S. national phase of International Patent Application No. PCT/JP2013/080296, filed Nov. 8, 2013, which claims the benefit of Japanese Patent Application No. 2012-247896, filed on Nov. 9, 2012, which are incorporated by reference in their entireties herein.

INCORPORATION-BY-REFERENCE OF MATERIAL ELECTRONICALLY SUBMITED

Incorporated by reference in its entirety herein is a computer-readable nucleotide/amino acid sequence listing submitted concurrently herewith and identified as follows: 3,344 bytes ASCII (Text) file named "720746SequenceListing.txt," created May 1, 2015.

TECHNICAL FIELD

The present invention relates to a test method for determining a lesion site of nephritis by using Fibroblast-specific protein 1 (hereinafter FSP1), comprising comparing a concentration of monomer FSP1 and a concentration of multimer FSP1 contained in a biological sample derived from the test subject, a reagent for performing the test, and the like.

BACKGROUND ART

FSP1 is a protein identified as a marker specific to fibroblast (non-patent document 1), and encodes a filament-bound S100A4 protein having an EF hand binding domain (non-patent document 2). The present inventors found that promoted expression of FSP1 is seen in podocytes and crescent cells in active glomerular diseases such as crescentic glomerulonephritis and the like (non-patent document 3), and urinary FSP1 of crescentic glomerulonephritis patients can be a biomarker of the diseases (non-patent document 4). Furthermore, they also found that urinary FSP1 can be a disease activity index since it shows a positive correlation with the frequency of appearance of glomerulus that forms a cellular crescent.

However, the correlation between FSP1 in a biological sample and renal disease has been verified only for crescentic glomerulonephritis, and there is no report yet on the relation between renal interstitial disease and FSP1 in a biological sample. In addition, a method of conveniently determining a lesion site in nephritis patients has still been demanded in clinical situations.

DOCUMENT LIST

Non-Patent Documents non-patent document 1: Struts et al., The Journal of Cell Biology, Vol. 130, 393-405, 1995
non-patent document 2: Okada et al., The American Physiological Society, Vol. 273, F563-574, 1997
non-patent document 3: Yamaguchi et al., American Journal of Kidney Diseases, Vol. 54, 653-664, 2009
non-patent document 4: Iwano et al., Journal of the American Society of Nephrology, Vol. 23, 209-214, 2012

SUMMARY OF THE INVENTION

Problems to be Solved by the Invention

A problem of the present invention is provision of a method of determining a lesion site of nephritis and a reagent for performing the determination.

Means of Solving the Problems

As a result of studies, the present inventors have found that FSP1 can be detected in a biological sample of a patient with an interstitial renal disease, and the FSP1 is dominantly of a multimer type. On the other hand, they have also found that FSP1 found in a biological sample of a patient with a crescentic glomerulonephritis is dominantly of a monomer type.

Based on these findings, the present inventors have conducted further studies and completed the present invention.

That is, the present invention provides the following.

[1] A test method for determining a lesion site of nephritis, comprising the following steps:
   (1) a step of measuring not less than two of a total FSP1 concentration, a concentration of monomer FSP1 and a concentration of multimer FSP1 in a biological sample derived from a test subject,
   (2) a step of comparing the concentration of monomer FSP1 and the concentration of multimer FSP1 of the biological sample derived from the test subject.
[2] The test method of [1], wherein the biological sample is a urine sample.
[3] The test method of [1] or [2], wherein the measurement of the total FSP1 concentration, the concentration of monomer FSP1 and the concentration of multimer FSP1 is performed by an immunochemical measurement method.
[4] The test method of any one of [1]-[3], wherein the lesion site of nephritis to be determined is glomerulus or interstitial tissue.
[5] A reagent for determining a lesion site of nephritis, comprising at least one kind of FSP1-specific antibody.
[6] The reagent of [5], wherein the lesion site of nephritis to be determined is glomerulus or interstitial tissue.

EFFECT OF THE INVENTION

The test method and the reagent therefor of the present invention can render determination of a lesion site of a nephritis patient or a test subject suspected to have nephritis rapid and convenient.

BRIEF DESCRIPTION OF THE DRAWINGS

FIG. 1 shows an epitope mapping of F1-2 antibody and I11-23 antibody. 1: a sequence corresponding to the 1st-12th amino acids of the amino acid sequence shown in SEQ ID NO: 2, 2: a sequence corresponding to the 4th-15th amino acids of the amino acid sequence shown in SEQ ID NO: 2, 3: a sequence corresponding to the 7th-18th amino acids of the amino acid sequence shown in SEQ ID NO 2, 4: a sequence corresponding to the 10th-21st amino acids of the amino acid sequence shown in SEQ ID NO: 2, 5: a sequence corresponding to the 68th-79th amino acids of the amino acid sequence shown in SEQ ID NO: 2, 6: a sequence corresponding to the 71st-82nd amino acids of the amino acid sequence shown in SEQ ID NO: 2, 7: a sequence corresponding to the 74th-85th amino acids of the amino acid sequence shown in SEQ ID NO: 2, 8: a sequence corresponding to the 77th-88th amino acids of the amino acid sequence shown in SEQ ID NO: 2, 9: a sequence corresponding to the 80th-92nd amino acids of the amino acid sequence shown in SEQ ID NO: 2.

DESCRIPTION OF EMBODIMENTS

Figure 2:
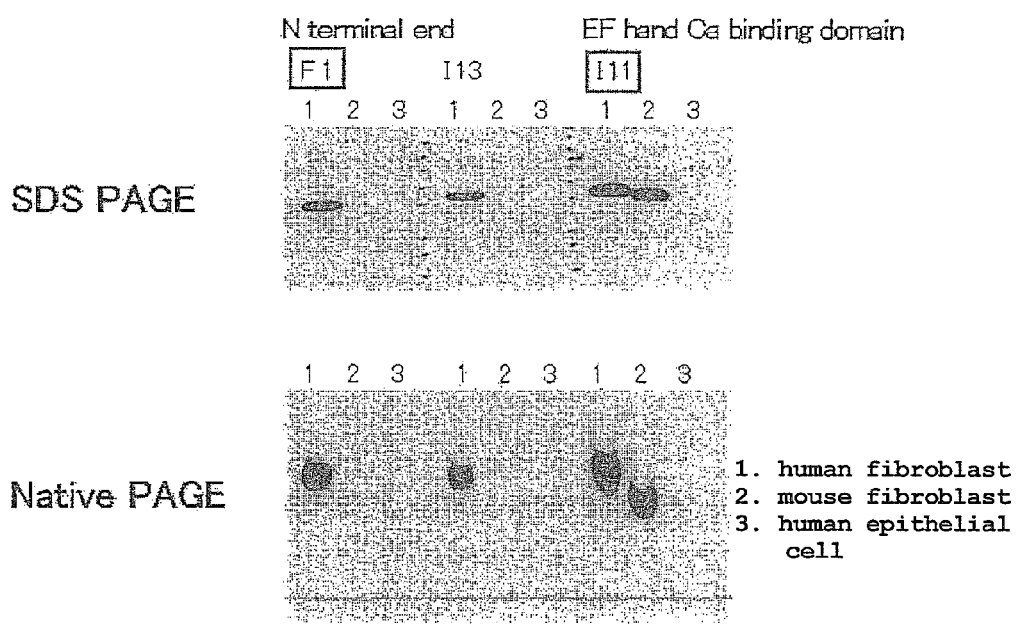
FIG. 2 shows that the epitope regions for human FSP1 that are recognized by F1-2 antibody and I11-23 antibody are different. F1 shows an F1-2 monoclonal antibody. I11 shows a I11-23 monoclonal antibody. Respective lanes show electrophoresis of human fibroblast extract, mouse fibroblast extract, and human epithelial cell extract. F1-2 antibody recognizes N-terminal having low molecular homology between human FSP1 and mouse FSP1, and I11 antibody recognizes EF hand domain showing high molecular homology between human FSP1 and mouse FSP1. The recognition site of I13 antibody is considered to be the same as that of F1-2 antibody.

The present invention provides a test method for determining a lesion site of nephritis by using a biological sample derived from a test subject.

While the test subject to whom the test method of the present invention is applicable is not particularly limited, examples thereof include patients clinically determined to be nephritis patients but having an unidentifiable lesion site, test subjects suspected to have developed nephritis and the like. The lesion site of nephritis determined by the test method of the present invention includes glomerulus (i.e., glomerular lesion) and interstitial tissue (i.e., interstitial lesion). The glomerular lesion determined in the present invention is a glomerular lesion characteristically containing monomer FSP1 in a biological sample, and a highly active glomerular lesion is more suitable for the determination. As used herein, high activity of glomerular lesion refers to a state where formation of crescent in glomerulus, growth of mesangial cells, or infiltration of T cells or macrophages into glomerulus is observed. Examples of such lesion include crescentic glomerulonephritis, IgA nephropathy, lupus nephritis, purpura nephritis and the like. The interstitial lesion determined in the present specification is an interstitial lesion characteristically having multimer FSP1 in a biological sample, and a highly active interstitial lesion is more suitable for the determination. Here, high activity of interstitial lesion refers to a state where infiltration of T cells and macrophages into interstitium is observed. As such interstitial lesion, interstitial nephritis, renal interstitial fibrosis and the like can be mentioned.

While the biological sample to be used for the test method of the present invention is not particularly limited as long as it is collected from the above-mentioned test subject, for example, one easily collected from a living body such as urine and the like and biological tissues can also be used as biological samples and, for example, kidney and the like can be mentioned. When urine is used as a biological sample, for example, spontaneous urine, catheter urine and the like can be mentioned. However, a urine sample suspected of urinary tract infection and gross hematuria are preferably excluded. While a urine sample may be directly used for the test, a pre-treatment such as centrifugation and the like to remove debris may also be performed. Furthermore, the sample may be collected from a test subject immediately before the test, or previously collected and cryopreserved.

The present inventors have found, as shown in the below-mentioned Examples, that FSP1 in urine is dominantly present as a monomer type in crescentic glomerulonephritis patients. Simultaneously, they have found that a concentration of FSP1 in urine is dominantly present as a multimer type in interstitial nephritis patients and renal interstitial fibrosis patients.

Accordingly, the test method for determining a lesion site of nephritis of the present invention comprises the following steps:

(1) a step of measuring not less than two of a total FSP1 concentration, a concentration of monomer FSP1 and a concentration of multimer FSP1 in a biological sample derived from a test subject, (2) a step of comparing the concentration of monomer FSP1 and the concentration of multimer FSP1 of the biological sample derived from the test subject.

In the present invention, the total FSP1 concentration refers to a concentration of an FSP1 protein containing monomer FSP1 and multimer FSP1 in a biological sample.

The measurement methods of the total FSP1 concentration, the concentration of monomer FSP1 and the concentration of multimer FSP1 in the present invention should not be particularly limited, and any measurement method can be used as long as it is a measurement method for detecting antigen level, antibody level or the level of antibody-antigen complex corresponding to antigen level in a biological sample by a chemical or physical means. Examples of such method include gel electrophoresis (e.g., SDS-PAGE, NATIVE-PAGE, 2D gel electrophoresis and the like), various separation and purification methods (e.g., ion exchange chromatography, hydrophobic chromatography, gel filtration chromatography, affinity chromatography, reversed-phase chromatography, isoelectric point chromatography, capillary electrophoresis and the like), ionization method (e.g., electron impact ionization method, field desorption method, secondary ionization method, fast atom bombardment method, matrix-assisted laser absorption/ionization (MALDI) method, electrospray method and the like), mass spectrometer (e.g., double-focusing mass spectrometer, quadrupole analyzer, time-of-flight mass spectrometer, Fourier-transform mass spectrometer, ion cyclotron mass spectrometer and the like) and the like. In the present invention, an immunochemical measurement method is also preferably performed.

In the present invention, FSP1 to be detected in a sample is of a monomer type or a multimer type (including multimer type of dimer or more). Examples of the monomer type FSP1 include a protein containing an amino acid sequence the same as or substantially the same as the amino acid sequence shown in SEQ ID NO: 2. Examples of the amino acid sequence substantially the same as the amino acid sequence shown in SEQ ID NO: 2 include an amino acid sequence having not less than about 70%, preferably not less than about 80%, more preferably not less than about 90%, particularly preferably not less than about 95%, most preferably not less than about 98%, homology with the amino acid sequence shown in SEQ ID NO: 2 and the like. The FSP1 of the present invention is preferably a protein having the amino acid sequence shown in SEQ ID NO: 2, namely, human FSP1.

The homology of the amino acid sequence in the present specification can be calculated, for example, using homology calculation algorithm NCBI BLAST (National Center for Biotechnology Information Basic Local Alignment Search Tool) under the following conditions (expectancy=10; gap allowed; matrix=BLOSUM62; filtering=OFF).

When an immunochemical measurement method is used in the step of measuring not less than two of a total FSP1 concentration, a monomer FSP1 concentration and a multimer FSP1 concentration, it is characterized by the use of an FSP1-specific antibody. Examples of the FSP1-specific antibody to be used in the present invention include an antibody that recognizes both monomer FSP1 and multimer FSP1, an antibody that recognizes only multimer FSP1, and an antibody that recognizes only monomer FSP1 in a biological sample.

Of the FSP1-specific antibodies used in the present invention, the antibody that recognizes both monomer FSP1 and multimer FSP1 can be used in a combination of two kinds that recognize different epitopes, as described in the below-mentioned immunochemical measurement method. Therefore, the epitopes recognized by respective antibodies are preferably located at distant positions on FSP1. Examples of such antibody include an antibody that recognizes EF hand calcium binding domain of FSP1 as an epitope, preferably an antibody that recognizes the amino acid sequence shown in SEQ ID NO: 4 as an epitope, and an antibody that recognizes the N-terminal amino acid sequence of FSP1, as an epitope, preferably an antibody that recognizes the amino acid sequence shown in SEQ ID NO: 3 as an epitope.

FSP1-specific antibodies of the present invention can be produced using an appropriate immunogen and by a known method. Examples of the immunogen include the full-length protein of FSP1 and a partial peptide thereof. The full-length protein of FSP1 used as an immunogen in the present invention is a protein as described above. The partial peptide of FSP1 used as an immunogen in the present invention is a peptide containing a partial amino acid sequence of the amino acid sequence the same as or substantially the same as the amino acid sequence shown in SEQ ID NO: 2.

Alternatively, the partial peptide of FSP1 used as an immunogen may be a peptide containing the N-terminal amino acid sequence of FSP1 or the EF hand calcium binding domain of FSP1. One embodiment of the N-terminal amino acid sequence of FSP1 is a peptide sequence containing, from the amino acid sequence shown in SEQ ID NO: 2, an amino acid sequence the same as or substantially the same as a sequence corresponding to the 1st-12th amino acids (SEQ ID NO: 3). One embodiment of the EF hand calcium binding domain of FSP1 is a peptide sequence containing, from the amino acid sequence shown in SEQ ID NO: 2, an amino acid sequence the same as or substantially the same as a sequence corresponding to the 80th-92nd amino acids (SEQ ID NO: 4).

FSP1 used as an immunogen can be produced from a cell or tissue of a mammal by a protein purification method known per se. Specifically, tissues or cells of a mammal are homogenized, soluble fraction and/or nuclear fraction are separated and purified by chromatography such as reversed-phase chromatography, ion exchange chromatography, affinity chromatography and the like, whereby FSP1 can be produced.

FSP1 or a partial peptide thereof used as an immunogen can also be produced according to a known peptide synthesis method.

The peptide synthesis method may be, for example, any of a solid phase synthesis process and a liquid phase synthesis process. A partial peptide or amino acid capable of constituting FSP1 to be used as an immunogen, and the remaining portion are condensed and, when the resultant product has a protecting group, the protecting group is removed, whereby the object protein can be produced.

Examples of the FSP1-specific antibody to be used in the present invention include one produced in the blood of an animal, one produced by hybridoma, one produced by a host transformed with an expression vector containing an antibody gene by a genetic engineering method, one produced by a cell containing an antibody gene screened for by a phage display method, a human antibody directly obtained from a transgenic mouse that produces a human antibody, and the like.

FSP1-specific antibody can be produced by those of ordinary skill in the art by a known method.

FSP1 is administered by itself or together with a carrier or a diluent to a mammal at a site where antibody production is possible by the administration. FSP1 to be used as an immunogen may be the aforementioned full-length protein of FSP1, or a partial peptide thereof (where necessary, a complex crosslinked with a carrier protein such as bovine serum albumin, KLH (Keyhole Limpet Hemocyanin) and the like). In administration, complete Freund's adjuvant or incomplete Freund's adjuvant may be administered to enhance the antibody producing capacity. Examples of the mammal to be used include monkey, rabbit, dog, guinea pig, mouse, rat, sheep and goat, with preference given to mouse and rat.

In the production of hybridoma, a mammal immunized with an antigen, for example, an individual having a confirmed antibody titer is selected from mice, spleen or lymph node is removed 2-5 days after the final immunization, and antibody-producing cells contained therein are fused with myeloma cells, whereby a monoclonal antibody-producing hybridoma can be prepared.

While various methods can be used for screening for a monoclonal antibody-producing hybridoma, for example, a method including adding hybridoma culture supernatant to a solid phase (e.g., microplate) to which FSP1 has been adsorbed directly or together with a carrier, adding an anti-immunoglobulin antibody (when cell used for cell fusion is from mouse, anti-mouse immunoglobulin antibody is used) labeled with a radioactive substance, an enzyme and the like or protein A, and detecting the monoclonal antibody bound to the solid phase, a method including adding hybridoma culture supernatant to a solid phase to which an anti-immunoglobulin antibody or protein A has been adsorbed, adding FSP1 labeled with a radioactive substance, an enzyme and the like, and detecting the monoclonal antibody bound to the solid phase, and the like can be mentioned.

A monoclonal antibody can be separated and purified according to an immunoglobulin separation and purification method [e.g., salting out method, alcohol precipitation method, isoelectric point precipitation method, electrophoresis, adsorption and desorption method by an ion exchanger (e.g., DEAE), ultracentrifugation method, gel filtration method, antigen bound solid phase or a specific purification method including collecting antibody alone by an active adsorbent such as protein A or protein G and the like, and dissociating the bond to give an antibody], like general separation and purification of polyclonal antibody.

Using the FSP1-specific antibodies obtained as above, total FSP1 concentration, concentration of monomer FSP1 and concentration of multimer FSP1 in a biological sample derived from the test subject can be each measured by an immunochemical measurement method. Specifically, for example, it can be performed as follows.

(1) Sandwich ELISA Method, Immunochromatography, Agglutination Method

An immobilized FSP1-specific antibody is reacted with a test solution containing a biological sample (primary reaction), a labeled FSP1-specific antibody which is the same as or different from the immobilized FSP1-specific antibody, is reacted (secondary reaction), and the activity of the labeled form is measured, whereby total FSP1 level, multimer FSP1 level or monomer FSP1 level of the test solution can be quantified.

The immobilized FSP1-specific antibody may be any of an antibody that recognizes both monomer FSP1 and multimer FSP1, an antibody that recognizes only multimer FSP1, and an antibody that recognizes only monomer FSP1. As a solid-phased carrier, microplate well, nitrocellulose membrane, latex beads, magnetic beads and the like can be used. The method of forming a solid phase may be physical adsorption, or imparting orientation by a chemical bond and the like. The immobilization may be performed in advance before primary reaction or after forming a sandwich complex.

A labeled FSP1-specific antibody is used by binding a labeled form capable of detecting an antigen antibody reaction product. The labeled antibody may be an antibody the same as or different from an immobilized FSP1-specific antibody. As the labeled form, radioisotope, gold colloid, enzyme, fluorescent substance, luminescence substance, enzyme substrate and the like can be used. In addition, the labeled form may be a substance that indirectly enables detection. As a method for indirectly enabling detection, for example, streptavidin=biotin reaction, sugar chain=lectin reaction, nuclear magnetic resonance reaction and the like can be mentioned. Alternatively, when a solid phase used for immobilized FSP1-specific antibody is latex bead or magnetic bead, FSP1-specific antibody used for the secondary reaction may be also solid phased using latex bead or magnetic bead to coagulate sandwich complex, and the turbidity of the aggregate itself may be utilized for the detection.

A sandwich complex composed of multimer FSP1 and/or monomer FSP1 and FSP1-specific antibody in a biological sample is selected by a step for removing a substance that non-specifically reacted with the antibody and unreacted antibodies. As a removal method, a washing step with a buffer containing a detergent and the like, a separation step using a magnet or electric chemical properties, or a separation step based on the difference in mobility such as molecular sieve and chromatography are considered; however, the method may be any as long as it can specifically leave an immunocomplex alone.

Using any of the above-mentioned detection means, an immunocomplex can be measured. The level of an immunocomplex is determined by, for example, absorbance, fluorescence intensity, luminescence intensity and the like. Separately, quantification based on a comparison of the level of immunocomplex with that of FSP1 having a known concentration, or the intensity thereof may be simply compared qualitatively.

When immobilized FSP1-specific antibody and labeled FSP1-specific antibody are antibodies recognizing both different monomer FSP1s and multimer FSP1s (e.g., when one antibody is an antibody that recognizes EF hand calcium binding domain of FSP1 as an epitope, and the other antibody is an antibody that recognizes the N-terminal amino acid sequence of FSP1 as an epitope), FSP1 detected by the above-mentioned measurement method can detect both multimer FSP1 and monomer FSP1 in a biological sample. In such case, using the same antibody as the immobilized FSP1-specific antibody and the labeled FSP1-specific antibody (e.g., an antibody that recognizes EF hand calcium bond domain of FSP1 as an epitope), multimer FSP1 alone can be detected and the monomer FSP1 can be calculated. Alternatively, using an antibody that recognizes only multimer FSP1 or an antibody that recognizes only monomer FSP1 as an immobilized FSP1-specific antibody, multimer FSP1 or monomer FSP1 can also be detected directly.

(2) Competitive Method

A measurement method based on the above-mentioned sandwich ELISA method and the like as a measurement principle may be a method based on, as a measurement principle, a competitive method using FSP1-specific antibodies alone, one or both of which recognize only one kind of multimer FSP1 or monomer FSP1. In this case, FSP1 in a biological sample can be measured by labeling FSP1 or a substance having antigenicity equivalent thereto (partial peptide of FSP1) as an antigen with radioisotope, gold colloid, enzyme, fluorescent substance, luminescence substance, enzyme substrate and the like, and having an antibody recognizing only multimer FSP1 or an antibody recognizing only monomer FSP1 and solid-phased on microplate well, nitrocellulose membrane, latex beads, magnetic beads and the like compete with FSP1 in a biological sample.

(3) Absorption Method

In a measurement method using the above-mentioned sandwich ELISA method or competitive method, an antibody that recognizes only multimer FSP1 or an antibody that recognizes only monomer FSP1 and the like is used, a step of absorbing or removing either one of multimer FSP1 and monomer FSP1 in a biological sample by the antibody and the like is performed in advance, and FSP1 is measured, whereby only FSP1 left unremoved can also be measured.

Application of the test method of the present invention does not require setting of special conditions, operation and the like. The measurement system of FSP1 can be constructed by adding general technical consideration of those of ordinary skill in the art to general conditions and operation method of each method. Compendia, books and the like can be referred to for the detail of such general technical means. For example, Hiroshi Irie ed., "Radioimmunoassay" (Kodansha, published in 1974), Hiroshi Irie ed., "Supplementary volume of Radioimmunoassay" (Kodansha, published in 1979), Eiji Ishikawa et al. ed., "Enzyme Immunoasssay" (Igaku-Shoin, published in 1978), Eiji Ishikawa et al. ed., "Enzyme Immunoasssay" (2nd edition) (Igaku-Shoin, published in 1982), Eiji Ishikawa et al. ed., "Enzyme Immunoasssay" (3rd edition) (Igaku-Shoin, published in 1987), "Methods in ENZYMOLOGY" Vol. 70 (Immunochemical Techniques (Part A)), ibidem Vol. 73 (Immunochemical Techniques (Part B)), ibidem Vol. 74 (Immunochemical Techniques (Part C)), ibidem Vol. 84 (Immunochemical Techniques (Part D: Selected Immunoassays)), ibidem Vol. 92 (Immunochemical, Techniques (Part E: Monoclonal Antibodies and General Immunoassay Methods)), ibidem Vol. 121 (Immunochemical Techniques (Part I: Hybridoma Technology and Monoclonal Antibodies)) (all published by Academic Press) and the like can be referred to.

As shown in the below-mentioned Examples, comparing crescentic glomerulonephritis patient having highly active glomerular lesion and interstitial nephritis or renal interstitial fibrosis patients having highly active interstitial lesion, urinal FSP1 is dominantly present as a monomer type in crescentic glomerulonephritis patients. In addition, urinal FSP1 shows positive correlation with emergence frequency of glomerulus showing cellular crescent formation. On the other hand, urinal FSP1 is dominantly present as a multimer type in interstitial nephritis or renal interstitial fibrosis patients. Therefore, a test method for determination of a lesion site of nephritis is performed based on such positive correlation between the concentration of monomer FSP1 and the morbidity rate of the glomerular lesion, or the concentration of multimer FSP1 and the morbidity rate of the interstitial lesion.

For example, a concentration of monomer FSP1 and a concentration of multimer FSP1 in a biological sample from a test subject are compared. Alternatively, a correlation figure between a concentration of monomer FSP1 and a concentration of multimer FSP1, and the presence or absence of affection with glomerular lesion and interstitial lesion is drawn in advance, and the concentrations of the monomer FSP1 and multimer FSP1 of the test subject may be compared with the correlation figure. The concentrations are preferably compared based on the presence or absence of a significant difference.

When the concentration of monomer FSP1 is higher than the concentration of multimer FSP1 in the test subject (not less than 51% of the total of the concentration of monomer FSP1 and the concentration of multimer FSP1), it is determined that the lesion site of nephritis is highly possibly glomerulus, and when the concentration of multimer FSP1 is higher than the concentration of monomer FSP1 (not less than 51% of the total of a concentration of monomer FSP1 and a concentration of multimer FSP1), the lesion site of nephritis is highly possibly interstitial tissue. When the concentration is similar to the concentration in a biological sample of patients wherein the lesion site of nephritis is glomerulus or interstitial tissue, it is determined that the lesion site of nephritis is highly possibly glomerulus or interstitial tissue.

The present invention further provides a test reagent for determination of a lesion site of nephritis. The reagent of the present invention may be a reagent for conveniently performing the aforementioned test method of the present invention, and is not particularly limited. The reagent for the test comprises an FSP1-specific antibody. Examples of the FSP1 antibody include an antibody that recognizes both monomer FSP1 and multimer FSP1, an antibody that recognizes only multimer FSP1, and an antibody that recognizes only monomer FSP1, and the FSP1 antibody preferably contains one or more kinds of those antibodies. Examples of the FSP1-specific antibody in the present invention include those recited for the above-mentioned test method.

The FSP1-specific antibody of the present invention can be provided in a state of being dissolved in water or a suitable buffer. Alternatively, the FSP1-specific antibody of the present invention can also be provided in a state of being immobilized on a suitable solid phase. Examples of the solid phase include, but are not limited to, microplate well, nitrocellulose membrane, latex beads, magnetic beads and the like. The FSP1-specific antibody of the present invention can be provided in a state of being labeled in advance with the above-mentioned labeling substance, or may be provided separately from the labeling substance and labeled when in use.

The reagent of the present invention is other substance necessary, in addition to the aforementioned antibody, for a reaction to measure the concentration of monomer FSP1 or the concentration of multimer FSP1, and that does not adversely influence the reaction even when it is preserved concurrently. Alternatively, the reagent may be provided together with other reagent containing other substance necessary for a reaction to detect FSP1. Examples of other substance to detect FSP1 include reaction buffer, blocking solution, enzyme substrate, nonspecific reaction inhibitor, preservative, detergent and the like.

EXAMPLES

The present invention is explained in more detail in the following by referring to Examples, which are clearly not to be construed as limitative.

Example 1

Obtainment of Monoclonal Antibody to FSP1 and Epitope Mapping

A full-length human FSP1 gene was inserted into a pET-49b(+) vector (Novagen) having a GST tag sequence and a His tag sequence to prepare an FSP1 expression vector. BL21DE3 competent cells were transformed with the vector, and expression of protein was induced using isopropyl-β-D-thiogalactopyranoside (Takara Bio Inc.). The expressed fusion protein was purified by column chromatography using a HisTrap HP column (GE Healthcare), and GST tag and His tag were cleaved by human rhino virus 3C protease (Novagen) to give a purified recombinant human FSP1 (rFSP1). rFSP1 (50 µg/250 µl) was emulsified in an equal amount of CFA (Difco Laboratories), and used as an antigen.

To produce monoclonal antibodies, an antigen was intraperitoneally administered to BALB/c mouse (female, 7-week-old) (CLEA Japan Inc.), and similar immunization was performed 2 weeks, 4 weeks, and 6 weeks later. One week from the 4th immunization, the antigen without adjuvant was additionally injected into the tail vein. Three days from the additional injection, the spleen was isolated from the mouse, passed through a 100-mesh steel net to allow for dissociation. The dissociated splenocytes ($2\times10^8$) were fused with the same number of myeloma cells in the presence of 50% polyethylene glycol (Roche Applied Science). The fused cells were suspended in a selection growth medium containing 5% Briclone (Archport), seeded on 96 well culture plates ($2\times10^5$ cells/well) and cultured while regularly exchanging the medium. The supernatant of wells containing hybridoma colony were screened for the presence of a particular antibody by direct ELISA, and hybridoma cells derived from positive wells were cloned twice by limiting dilution. Each clone was cultured in a medium, antibody-rich supernatant was concentrated by ammonium sulfate precipitation, dialyzed against PBS, and preserved at −80° C.

Supernatant was collected from 484 wells containing hybridoma cells, and detection of antibody was tried. Using direct ELISA and native PAGE, 5 antibodies were found to bind to rFSP1. Of these five clones, two kinds of antibodies (F1-2 and I11-23) having a high titer to bind to rFSP1 were selected. In isotype analysis (AbD Serotec), F1-2 was found to belong to IgG2a(κ) subclass, and I11-23 was found to belong to IgG1(κ) subclass. In epitope mapping using PepSpots (JPT Peptide Technologies), these two monoclonal antibodies recognize different epitopes, F1-2 recognizes the N-terminal of FSP1 (a sequence corresponding to 1st-12th amino acids in the amino acid sequence shown in SEQ ID NO: 2; SEQ ID NO: 3), and I11-23 recognizes EF hand calcium binding domain (a sequence corresponding to 80th- 92nd amino acids in the amino acid sequence shown in SEQ ID NO: 2; SEQ ID NO: 4) (FIG. 1). In an epitope binding test using human FSP1 and mouse FSP1, F1-2 recognized N-terminal of FSP1, and I11-23 recognized SF hand calcium binding domain (FIG. 2).

Example 2

Figure 3:
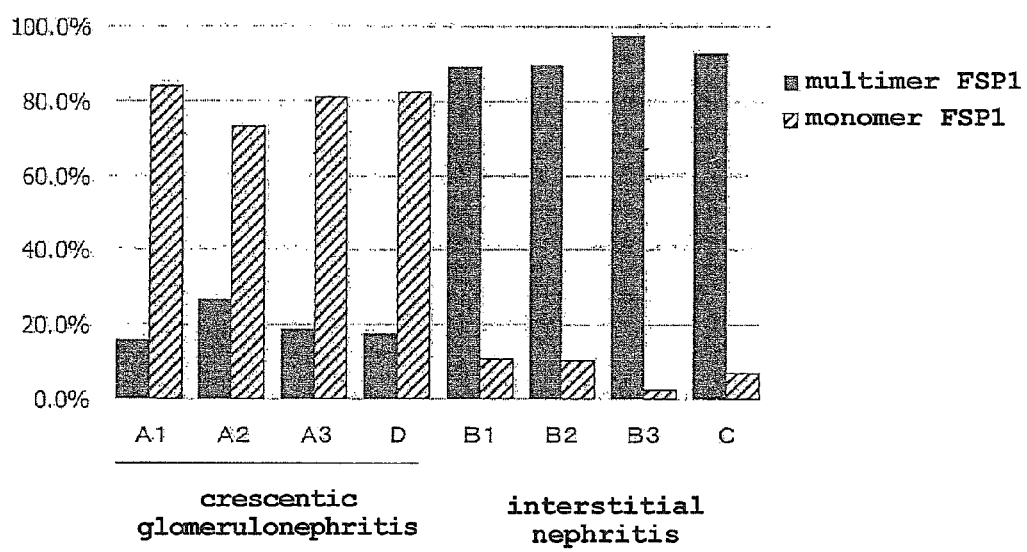
FIG. 3 is a graph showing the proportion (%) of a concentration of multimer FSP1 and a concentration of monomer FSP1 relative to the total FSP1 concentration in crescentic glomerulonephritis (A1-3, D) and interstitial nephritis (B1-3, C).

Measurement of Urinal FSP1 in Sample Derived from Renal Disease Patients by Sandwich ELISA Method Urine samples were collected from two patients with crescentic glomerulonephritis, one patient with interstitial nephritis, and one patient with renal interstitial fibrosis. Urine samples were independently collected 3 times from one of the two patients with crescentic glomerulonephritis and the interstitial nephritis patient. Urine samples were also collected from membranous nephropathy and nephrosclerosis showing low activity of glomerular lesion. The amount of FSP1 in a urine sample was measured by the sandwich ELISA method. I11-23 antibody purified from ascites antibodies was immobilized at an immobilization concentration of 1.25 μg/mL on each well of a 96 well microplate, and a sample (100 μL) 4-fold diluted from the collected urine sample was contacted with the well. After primary reaction at room temperature for 1 hr, the well was washed three times. Then, F1-2 antibody and I11-23 antibody purified from ascites antibodies were each labeled with HRP, and 2000-fold diluted labeled F1-2 antibody (100 μL) and 4000-fold diluted labeled I11-23 antibody (100 μL) were each contacted with the well. After secondary reaction at room temperature for 1 hr, the well was washed three times. A substrate solution (100 μL) was contacted with the well and the mixture was reacted at 37° C. for 30 min. A reaction quenching solution (100 μL) was contacted with the well to terminate the reaction, and the absorbance of the reaction mixture was measured. Using FSP1 at each concentration (0, 1, 2, 4, 8, 16, 32, 64 ng/mL) (100 μL) as a standard protein solution, a standard curve of the absorbance and FSP1 concentration was drawn in advance by the above-mentioned method, and based on the standard curve, each FSP1 concentration (ng/mL) was assumed from the absorbance of each sample obtained, and the difference thereof was also calculated (Table 1). Regarding crescentic glomerulonephritis as highly active glomerulonephritis (A1-3, D) and interstitial nephritis and renal interstitial fibrosis as highly active interstitial nephritis (B1-3, C), the proportion of the concentration of multimer FSP1 and the concentration of monomer FSP1 is shown in a graph (FIG. 3).

TABLE 1

| | antibody combination (target FSP1) | | |
|---|---|---|---|
| case | solid-phased I11-23 antibody and labeled F1-2 antibody (total FSP1) | solid-phased I11-23-antibody and labeled I11-23 antibody (multimer FSP1) | concentration difference (monomer FSP1) |
| A1 | 20.8 | 3.3 | 17.5 |
| A2 | 19.5 | 5.2 | 14.3 |
| A3 | 18.7 | 3.5 | 15.2 |
| B1 | 25.9 | 23.1 | 2.8 |
| B2 | 31.0 | 27.8 | 3.2 |
| B3 | 33.7 | 32.8 | 0.9 |
| C | 9.7 | 9.0 | 0.7 |
| D | 9.0 | 1.6 | 7.4 |
| E | 0.07 | 0.04 | 0.03 |
| F | 0.54 | 0.12 | 0.42 |
| G | 0.83 | 0.37 | 0.46 |
| H | 0.03 | 0.00 | 0.03 |
| I | 0.50 | 0.16 | 0.34 |

A1-3: crescentic glomerulonephritis, B1-3: interstitial nephritis, C: renal interstitial fibrosis, D: crescentic glomerulonephritis, E, F, G: membranous nephropathy, H, I: nephrosclerosis. Numerical values show FSP1 concentration (ng/mL).

As shown in Table 1 or FIG. 3, in patients with crescentic glomerulonephritis who are patients with a highly active glomerular lesion, the proportion of the concentration of monomer FSP1 was about 84.1% (A1), about 73.3% (A2), about 81.3% (A3), about 82.2% (D), respectively, when the total of the concentration of multimer FSP1 and the concentration of monomer FSP1 was 100%. On the other hand, in patients with interstitial nephritis or renal interstitial fibrosis who are patients with a highly active interstitial lesion, the proportion of the concentration of multimer FSP1 was about 89.2% (B1), about 89.7% (B2), about 97.3% (B3), about 92.8% (C), respectively, when the total of the concentration of multimer FSP1 and the concentration of monomer FSP1 was 100%. In glomerular lesion patients having low activity (E, F, G, H, I), the concentration of monomer FSP1 and the concentration of multimer FSP were both small, and leakage of FSP1 was small.

The results indicating detection of FSP1 by the solid phased I11-23 antibody and the labeled I11-23 antibody that recognize the same epitope suggest that multimer FSP1 is contained in the urine of patients with interstitial nephritis and renal interstitial fibrosis, which are interstitial lesions, and is dominant since its abundance ratio is higher than that of monomer FSP1. On the other hand, the results indicating detection of FSP1 by the solid phased I11-23 antibody and the labeled F1-2 antibody that recognize different epitopes suggest that monomer FSP1 is contained in the urine of patients with crescentic glomerulonephritis which is a glomerular lesion, and is dominant since its abundance ratio is higher than that of multimer FSP1. Therefore, it was confirmed whether FSP1 in a urine sample is dominant as a multimer or dominant as a monomer correlates with a lesion site of nephritis.

INDUSTRIAL APPLICABILITY

The test method and a reagent therefor of the present invention can rapidly and conveniently determine a lesion site of nephritis patients or test subjects suspected to have nephritis.

This application is based on a patent application No. 2012-247896 filed in Japan (filing date: Nov. 9, 2012), the contents of which are incorporated in full herein.

The invention claimed is:

1. A test method for determining a lesion site of nephritis, comprising the following steps:
   (1) a step of measuring the concentrations of two or three of (i) total Fibroblast-Specific Protein 1 (FSP1), (ii) monomer FSP1, and (iii) multimer FSP1 in a biological sample derived from a test subject,
   (2) a step of comparing the concentration of monomer FSP1 and the concentration of multimer FSP1 of the biological sample derived from the test subject
   (3) a step of determining that a lesion site of nephritis is glomerulus when FSP1 is dominantly present as a monomer type in the biological sample derived from the test subject, and, conversely, when FSP1 is dominantly present as a multimer type in the sample, the lesion site of nephritis is interstitial tissue.

2. The test method according to claim 1, wherein the biological sample is a urine sample.

3. The test method according to claim 1, wherein the measurement of the total FSP1 concentration, the concentration of monomer FSP1 and the concentration of multimer FSP1 is performed by an immunochemical measurement method.

4. The test method according to claim 1, wherein the total FSP1 concentration and the concentration of multimer FSP1 in the biological sample derived from the test subject are measured in step (1).

5. A kit for determining a lesion site of nephritis, comprising
   (a) a reagent for detecting both multimer Fibroblast-Specific Protein 1 (FSP1) and monomer FSP1, comprising an immobilized FSP1-specific antibody and a labeled FSP1-specific antibody, wherein the immobilized FSP1-specific antibody and the labeled FSP1-specific antibody recognize different epitopes in FSP1; and
   (b) a reagent for detecting multimer FSP1 alone, comprising an immobilized FSP1-specific antibody and a labeled FSP1-specific antibody, wherein the immobilized FSP1-specific antibody and the labeled FSP1-specific antibody are the same.

6. The kit according to claim 5, wherein the FSP1-specific antibody in the reagent (b) recognizes EF hand calcium binding domain of FSP1 as an epitope.

7. A kit for determining a lesion site of nephritis, comprising
   (a) a reagent for detecting both multimer Fibroblast-Specific Protein 1 (FSP1) and monomer FSP1, comprising an immobilized FSP1-specific antibody and a labeled FSP1-specific antibody, wherein one antibody is an antibody that recognizes EF hand calcium binding domain of FSP1 as an epitope, and the other antibody is an antibody that recognizes the N-terminal amino acid sequence of FSP1 as an epitope, and
   (b) a reagent for detecting multimer FSP1 alone, comprising an immobilized FSP1-specific antibody and a labeled FSP1-specific antibody, wherein the both antibodies recognize EF hand calcium binding domain of FSP1 as an epitope.

8. The kit according to claim 5, wherein the lesion site of nephritis to be determined is glomerulus or interstitial tissue.

9. The kit according to claim 7, wherein the lesion site of nephritis to be determined is glomerulus or interstitial tissue.

10. The test method according to claim 3, wherein the immunochemical measurement method is performed by using
    (a) a reagent for detecting both multimer FSP1 and monomer FSP1, comprising an immobilized FSP1-specific antibody and a labeled FSP1-specific antibody, wherein the immobilized FSP1-specific antibody and the labeled FSP1-specific antibody are different antibodies that recognize both monomer FSP1 and multimer FSP1, and
    (b) a reagent for detecting multimer FSP1 alone, comprising an immobilized FSP1-specific antibody and a labeled FSP1-specific antibody, wherein the immobilized FSP1-specific antibody and the labeled FSP1-specific antibody are the same.

11. The test method according to claim 10, wherein the FSP1-specific antibody in the reagent (b) recognizes EF hand calcium binding domain of FSP1 as an epitope.

12. The test method according to claim 3, wherein the immunochemical measurement method is performed by using
    (a) a reagent for detecting both multimer FSP1 and monomer FSP1, comprising an immobilized FSP1-specific antibody and a labeled FSP1-specific antibody, wherein one antibody is an antibody that recognizes EF hand calcium binding domain of FSP1 as an epitope, and the other antibody is an antibody that recognizes the N-terminal amino acid sequence of FSP1 as an epitope, and
    (b) a reagent for detecting multimer FSP1 alone, comprising an immobilized FSP1-specific antibody and a labeled FSP1-specific antibody, wherein the both antibodies recognize EF hand calcium binding domain of FSP1 as an epitope.

* * * * *

UNITED STATES PATENT AND TRADEMARK OFFICE
CERTIFICATE OF CORRECTION

PATENT NO. : 9,494,600 B2  
APPLICATION NO. : 14/440468  
DATED : November 15, 2016  
INVENTOR(S) : Iwano et al.

Page 1 of 1

It is certified that error appears in the above-identified patent and that said Letters Patent is hereby corrected as shown below:

In the Claims

Claim 7, Column 16, Line 20, "FSP1alone" should be "FSP1 alone"

Claim 10, Column 16, Line 32, "FSP1and" should be "FSP1 and"

Signed and Sealed this  
Fourth Day of April, 2017

Michelle K. Lee  
*Director of the United States Patent and Trademark Office*

SEQUENCE LISTING

<160> NUMBER OF SEQ ID NOS: 4

<210> SEQ ID NO 1
<211> LENGTH: 306
<212> TYPE: DNA
<213> ORGANISM: Homo sapiens
<220> FEATURE:
<221> NAME/KEY: CDS
<222> LOCATION: (1)..(306)

<400> SEQUENCE: 1

```
atg gcg tgc cct ctg gag aag gcc ctg gat gtg atg gtg tcc acc ttc      48
Met Ala Cys Pro Leu Glu Lys Ala Leu Asp Val Met Val Ser Thr Phe
1               5                   10                  15 cac aag tac tcg ggc aaa gag ggt gac aag ttc aag ctc aac aag tca      96
His Lys Tyr Ser Gly Lys Glu Gly Asp Lys Phe Lys Leu Asn Lys Ser
            20                  25                  30 gag cta aag gag ctg ctg acc cgg gag ctg ccc agc ttc ttg ggg aaa     144
Glu Leu Lys Glu Leu Leu Thr Arg Glu Leu Pro Ser Phe Leu Gly Lys
        35                  40                  45 agg aca gat gaa gct gct ttc cag aag ctg atg agc aac ttg gac agc     192
Arg Thr Asp Glu Ala Ala Phe Gln Lys Leu Met Ser Asn Leu Asp Ser
50                  55                  60 aac agg gac aac gag gtg gac ttc caa gag tac tgt gtc ttc ctg tcc     240
Asn Arg Asp Asn Glu Val Asp Phe Gln Glu Tyr Cys Val Phe Leu Ser
65                  70                  75                  80 tgc atc gcc atg atg tgt aac gaa ttc ttt gaa ggc ttc cca gat aag     288
Cys Ile Ala Met Met Cys Asn Glu Phe Phe Glu Gly Phe Pro Asp Lys
                85                  90                  95 cag ccc agg aag aaa tga                                             306
Gln Pro Arg Lys Lys
            100
```

<210> SEQ ID NO 2
<211> LENGTH: 101
<212> TYPE: PRT
<213> ORGANISM: Homo sapiens

<400> SEQUENCE: 2

```
Met Ala Cys Pro Leu Glu Lys Ala Leu Asp Val Met Val Ser Thr Phe
1               5                   10                  15

His Lys Tyr Ser Gly Lys Glu Gly Asp Lys Phe Lys Leu Asn Lys Ser
            20                  25                  30

Glu Leu Lys Glu Leu Leu Thr Arg Glu Leu Pro Ser Phe Leu Gly Lys
        35                  40                  45

Arg Thr Asp Glu Ala Ala Phe Gln Lys Leu Met Ser Asn Leu Asp Ser
    50                  55                  60

Asn Arg Asp Asn Glu Val Asp Phe Gln Glu Tyr Cys Val Phe Leu Ser
65                  70                  75                  80

Cys Ile Ala Met Met Cys Asn Glu Phe Phe Glu Gly Phe Pro Asp Lys
                85                  90                  95

Gln Pro Arg Lys Lys
            100
```

<210> SEQ ID NO 3
<211> LENGTH: 12
<212> TYPE: PRT
<213> ORGANISM: Homo sapiens

<400> SEQUENCE: 3

Met Ala Cys Pro Leu Glu Lys Ala Leu Asp Val Met

```
<210> SEQ ID NO 4
<211> LENGTH: 13
<212> TYPE: PRT
<213> ORGANISM: Homo sapiens

<400> SEQUENCE: 4

Ser Cys Ile Ala Met Met Cys Asn Glu Phe Phe Glu Gly
1               5                   10
```